United States Patent
Purtle et al.

(10) Patent No.: US 9,068,205 B2
(45) Date of Patent: Jun. 30, 2015

(54) PROCESSES AND SYSTEMS FOR DRY-MILLED CORN ETHANOL AND CORN OIL PRODUCTION WITH IMPROVED CARBON FOOTPRINT

(71) Applicants: Ian Purtle, Plymouth, MN (US); Luca Zullo, Excelsior, MN (US)

(72) Inventors: Ian Purtle, Plymouth, MN (US); Luca Zullo, Excelsior, MN (US)

(73) Assignee: Glenmore Consulting, LLC, Plymouth, MN (US)

( * ) Notice: Subject to any disclaimer, the term of this patent is extended or adjusted under 35 U.S.C. 154(b) by 43 days.

(21) Appl. No.: 13/680,108

(22) Filed: Nov. 18, 2012

(65) Prior Publication Data

US 2013/0130343 A1     May 23, 2013

Related U.S. Application Data

(60) Provisional application No. 61/561,906, filed on Nov. 20, 2011.

(51) Int. Cl.

| | |
|---|---|
| *F26B 7/00* | (2006.01) |
| *F02C 3/28* | (2006.01) |
| *C12P 7/14* | (2006.01) |
| *F26B 23/00* | (2006.01) |
| *F26B 23/02* | (2006.01) |
| *F26B 25/00* | (2006.01) |
| *A23K 1/06* | (2006.01) |
| *C11B 1/10* | (2006.01) |
| *C12P 7/06* | (2006.01) |
| *C11B 1/06* | (2006.01) |

(52) U.S. Cl.
CPC ... *C12P 7/14* (2013.01); *F26B 7/00* (2013.01); *F02C 3/28* (2013.01); *F26B 23/001* (2013.01); *F26B 23/022* (2013.01); *F26B 25/005* (2013.01); *Y02E 50/12* (2013.01); *Y02E 50/17* (2013.01); *A23K 1/06* (2013.01); *C11B 1/10* (2013.01); *C12P 7/06* (2013.01); *C11B 1/06* (2013.01)

(58) Field of Classification Search
None
See application file for complete search history.

(56) References Cited

U.S. PATENT DOCUMENTS 4,006,536 A * 2/1977 Meiners .................... 34/169

FOREIGN PATENT DOCUMENTS

WO    WO 2006113683 A2 * 10/2006

OTHER PUBLICATIONS

Christianson, DD; et al; "Supercritical Fluid Extraction of Dry-Milled Corn Germ with Carbon Dioxide" Journal of Food Science, 49, 229-232, 1984.*

* cited by examiner

*Primary Examiner* — Blaine Lankford
*Assistant Examiner* — David Berke-Schlessel
(74) *Attorney, Agent, or Firm* — O'Connor & Company

(57) ABSTRACT

The present invention improves corn dry milling in several ways. Integrated corn biorefinery processes are disclosed which can produce ethanol, edible corn oil, DDGS, solvent-extracted meal, power, and optionally crude corn oil, starting from corn. Some variations employ corn fractionation and edible corn oil recovery using liquid carbon dioxide, avoiding hazardous hydrocarbon-based solvents to produce edible corn oil. Some variations employ integration of gas-fired co-generation into the dry-milled corn ethanol plant to significantly reduce energy usage and carbon footprint associated with the overall process. Counter-current drying is preferably employed to produce a high-quality DDGS product with high protein content, low mycotoxin content, and low residual ethanol content.

10 Claims, 3 Drawing Sheets

PROCESSES AND SYSTEMS FOR DRY-MILLED CORN ETHANOL AND CORN OIL PRODUCTION WITH IMPROVED CARBON FOOTPRINT

PRIORITY DATA

This patent application claims priority to U.S. Provisional Patent App. No. 61/561,906, filed Nov. 20, 2011, which is hereby incorporated by reference herein in its entirety.

FIELD OF THE INVENTION

The present invention generally relates to processes, systems, and apparatus for the conversion of corn into ethanol (or other fermentation products), corn oil, and other co-products.

BACKGROUND OF THE INVENTION

Increasingly, renewable liquid biofuels are being evaluated on their carbon footprint measured in grams of carbon dioxide equivalent per megajoule of energy content (g $CO_{2e}$/MJ), which is then compared to the same metric for the fossil fuels (gasoline-diesel fuel), which they are intended to replace.

The United States has invested heavily to build a renewable liquid-fuel industry that is largely based on the production of ethanol from dry-milled corn. This large industry uses around 40% of the U.S. corn crop to produce 15 billion gallons per year of corn-derived ethanol, which is the federal government's target production for 2015.

Nonetheless, there is continuing pressure on this large, well-established industry to continue to lower its carbon footprint. The industry continues to use relatively energy inefficient unit operations; for example, the conventional method of drying distillers' dried grains with solubles (DDGS) is a very inefficient single-pass rotary-drying system. Further, because the drying of DDGS involves the removal of residual ethanol, that ethanol vapor is usually emitted to the atmosphere as a volatile organic compound (VOC), which adversely impacts air quality.

To minimize the risk of high VOC emissions, the U.S. federal Environmental Protection Agency (EPA) has mandated the inclusion of a regenerative thermal oxidizer (RTO) to burn the exhaust from the DDGS dryer to eliminate the risk of VOC emissions. The RTO needs to burn a significant amount of natural gas in the process of destroying the residual ethanol vapor. It would be desirable to avoid the need for a RTO in an integrated system.

Compared to corn wet milling, corn dry milling has historically focused on ethanol production. There are several market drivers to improve corn dry milling and utilize principles of integrated biorefineries, including multiple co-products, efficient recycling, and energy integration. One need is to produce more edible corn oil than conventional processes. There is also a desire to avoid the use of hazardous hydrocarbon-based solvents to produce edible corn oil. Another need is to reduce the amount of residual ethanol in the DDGS co-product.

Most importantly, from the viewpoint of overall sustainability, what is needed is a process of corn dry milling that significantly reduces energy usage and lowers (fuel) ethanol's carbon footprint.

SUMMARY OF THE INVENTION

In some variations, this invention provides a process for producing ethanol, corn oil, and DDGS from corn, the process comprising:

(a) introducing corn to a corn fractionation unit configured to substantially separate the germ and the bran from the endosperm, to generate a starch stream containing up to 98% of the starch contained in the corn;

(b) introducing at least a portion of the starch stream, in the form of an aqueous slurry, to a saccharification unit configured to hydrolyze the starch into glucose;

(c) introducing at least a portion of the glucose to an aqueous fermentor containing a microorganism to ferment glucose into dilute ethanol and carbon dioxide;

(d) introducing the dilute ethanol to a distillation unit configured to generate an ethanol-rich distillate (overhead) and a solids-rich still residue (still bottoms);

(e) introducing the ethanol-rich distillate to an ethanol drying unit configured to generate anhydrous ethanol;

(f) optionally capturing at least a portion of the carbon dioxide from step (c) and liquefying the portion of the carbon dioxide to generate liquid carbon dioxide;

(g) introducing at least a portion of the germ, or a conditioned form thereof, to an extraction unit configured to extract edible crude corn oil using a solvent comprising the liquid carbon dioxide; and (h) drying the solids contained in the solids-rich still bottoms using a vertically stacked counter-current dryer, to generate distillers' dried grains with solubles (DDGS); and (i) recovering the anhydrous ethanol, the edible crude corn oil, and the DDGS.

In some embodiments, the starch stream in step (a) contains up to 95%, 98%, or more of the starch contained in the corn. The process may further include grinding extracted germ to generate a solvent-extracted meal. Optionally, at least a portion of the bran may be blended with the solids-rich still bottoms prior to, or during, step (h).

The extraction unit may utilize mechanical pressing. For example, the extraction unit may be a high-pressure, continuous screw press with one or more injection ports for introducing the liquid carbon dioxide. In some embodiments, the solvent in step (g) consists essentially of liquid carbon dioxide, which may be derived from the fermentation. In other embodiments, the solvent in step (g) comprises the liquid carbon dioxide from step (f) as well as another source of fresh or recycled carbon dioxide.

In some embodiments, the edible crude corn oil contains about 100 ppm or less phospholipids, such as less than about 50 ppm or less than about 20 ppm or less phospholipids.

In preferred embodiments, in step (a), mycotoxins that are present in the corn, if any, are concentrated in the bran. The process may be controlled so that the DDGS contains mycotoxins in an amount below a selected mycotoxin concentration.

Various recycle and integration schemes are disclosed herein. In some embodiments, at least a portion of exhaust gases from the counter-current dryer are condensed and recovered or recycled. Water may be recycled back to step (b) and/or step (c). Ethanol may be recovered and optionally recycled back to step (d) and/or step (e). Ethanol recovery increases the overall ethanol yield from the process.

Other variations of the invention provide a process for producing DDGS from still bottoms obtained from corn dry milling, the process comprising:

(a) providing or receiving a solids-rich still bottoms obtained from a distillation unit configured for purifying a fermentation product from fermentation of corn starch-derived glucose;

(b) optionally removing some liquid from the still bottoms, prior to drying;

(c) drying the still bottoms using a drying gas comprising air in a vertically stacked counter-current dryer, to generate a dried solids stream;

(d) cooling the dried solids stream using a cooling gas comprising air to generate a cooled solids stream comprising distillers' dried grains with solubles (DDGS); and (e) recovering the DDGS.

The fermentation product may be selected from the group consisting of alcohols, organic acids, amino acids, enzymes, microorganisms, and combinations thereof In some embodiments, the vertically stacked counter-current dryer utilizes superheated air to dry the still bottoms. The counter-current dryer may be disposed in a vertically stacked dryer/cooler combination. Exhaust gases from the counter-current dryer may be condensed and recovered or recycled. For example, water may be recycled within the corn dry milling process, for any water needs.

In some embodiments of the process for producing DDGS from still bottoms, the process further comprises recovering crude corn oil, such as inedible corn oil. In certain embodiments, the process includes the additional steps of:

(f) introducing the still bottoms to a first centrifuge to generate a first solids stream and a thin stillage;

(g) optionally introducing at least a portion of the thin stillage to a second centrifuge to generate an oil phase and an aqueous phase, wherein the oil phase comprises crude corn oil;

(h) introducing the aqueous phase from step (g) to an evaporator to generate a second solids stream and a water stream, wherein the water stream is optionally recycled; and (i) combining the first solids stream with the second solids stream, prior to or during step (c), whereby the combined solids stream is dried in the vertically stacked counter-current dryer, to produce the dried solids stream.

In some embodiments, the DDGS has a lower residual ethanol content compared to an otherwise-identical process without the vertically stacked counter-current dryer.

Other variations of this invention provide a process for producing DDGS and power from still bottoms solids obtained from corn dry milling, comprising:

(a) providing or receiving still bottoms solids obtained from separation (e.g., centrifugation) of a solids-rich still bottoms from a distillation unit configured for purifying a fermentation product from fermentation of corn starch-derived glucose;

(b) drying the still bottoms solids using a drying gas comprising air in a vertically stacked counter-current dryer, to generate a dried solids stream;

(c) optionally drying evaporated thin stillage using the drying gas in the vertically stacked counter-current dryer, to contribute to the dried solids stream;

(d) cooling the dried solids stream using a cooling gas comprising air to generate a cooled solids stream comprising distillers' dried grains with solubles (DDGS);

(e) introducing non-condensable exhaust gases from the counter-current dryer to a gas turbine;

(f) introducing a first fuel to the gas turbine under effective combustion conditions in the presence of oxygen derived at least in part from the drying gas introduced in step (b) and/or the cooling gas introduced in step (d), to generate power and heat;

(g) conveying hot exhaust gases from the gas turbine to a heat-recovery boiler for generating steam;

(h) optionally introducing a second fuel to the heat-recovery boiler; and (i) recovering the DDGS and the power.

In some embodiments, the counter-current dryer is disposed in a vertically stacked dryer/cooler combination. The vertically stacked counter-current dryer may utilize superheated air to dry still bottoms solids. The first and second fuels are preferably natural gas, although other fuels may be utilized.

In some embodiments, at least a portion of the steam is exported (to a user outside of the process). The gas turbine is preferably connected to a generator for generating electricity, a portion of which may be exported (to a user outside of the process).

Some embodiments further comprise a stack gas heat-recovery unit downstream of the heat-recovery boiler. In certain embodiments, substantially no volatile organic compounds escape the process. The process does not require a regenerative thermal oxidizer.

Integrated processes for corn dry milling may thus produce power, a fermentation product (such as ethanol, isobutanol, or 1-butanol), edible corn oil, and DDGS from corn, using one or more of the disclosed processes and systems or apparatus configured for carrying out such processes.

Figure 1:
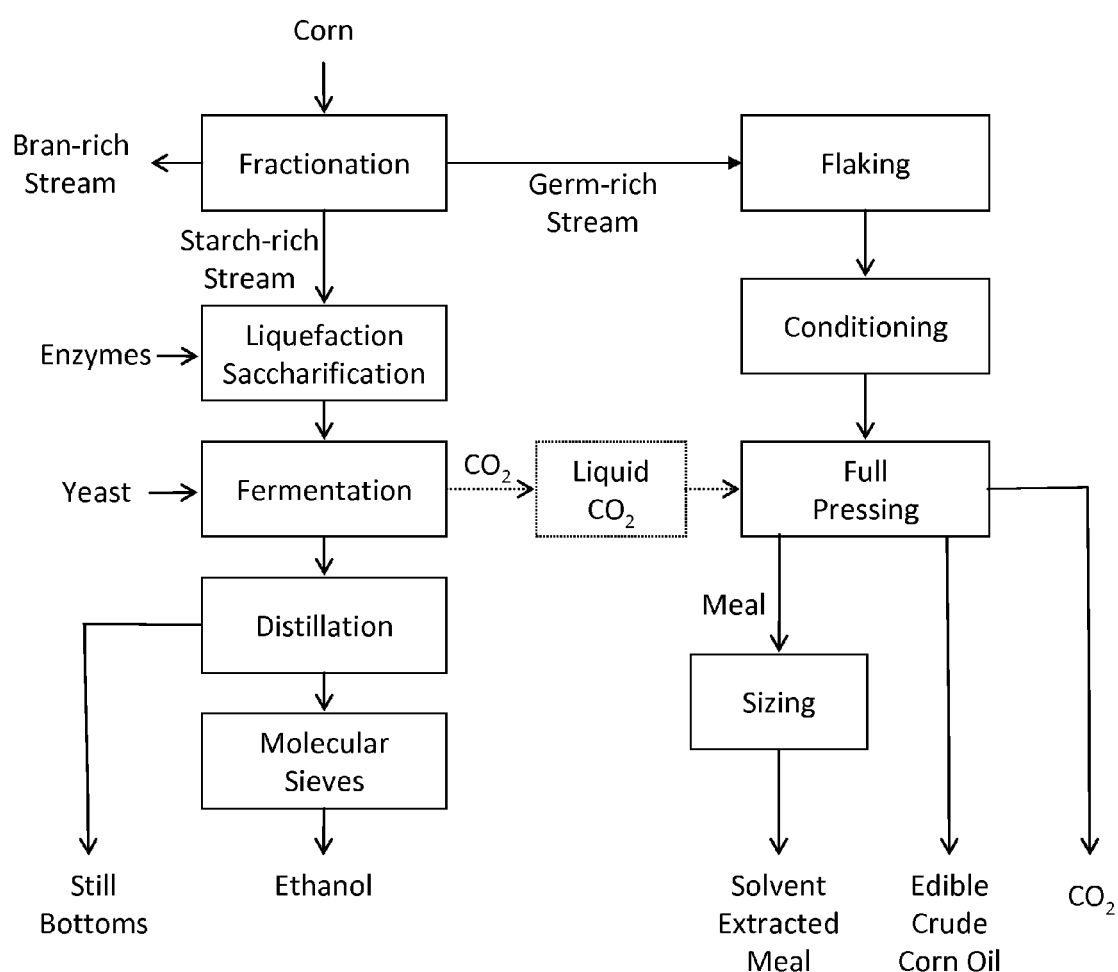
FIG. 1 depicts some variations of the invention for integration of corn fractionation, liquefying carbon dioxide from fermentation to ethanol, and edible crude corn oil recovery.

These and other embodiments, features, and advantages of the present invention will become more apparent to those skilled in the art when taken with reference to the following detailed description of the invention. Dotted lines indicate optional streams or unit operations. All figures are exemplary and not intended to limit the scope of the invention.

DETAILED DESCRIPTION OF EMBODIMENTS OF THE INVENTION

Certain embodiments of the present invention will now be further described in more detail, in a manner that enables the claimed invention so that a person of ordinary skill in this art can make and use the present invention.

Unless otherwise indicated, all numbers expressing reaction conditions, concentrations, yields, and so forth used in the specification and claims are to be understood as being modified in all instances by the term "about." Accordingly, unless indicated to the contrary, the numerical parameters set forth in the following specification and attached claims are approximations that may vary depending at least upon the specific analytical technique. Any numerical value inherently contains certain errors necessarily resulting from the standard deviation found in its respective testing measurements.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. If a definition set forth in this section is contrary to or otherwise inconsistent with a definition set forth in patents, published patent applications, and other publications that are incorporated by reference, the definition set forth in this specification prevails over the definition that is incorporated herein by reference.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of."

In some variations, this invention provides an integrated approach to significantly and substantially reduce the grams of carbon dioxide equivalent per megajoule of energy content ($g\ CO_{2e}/MJ$) for the production of ethanol via corn dry milling, which is the predominant method of ethanol production in the United States today.

In some variations, this invention provides an integrated approach to lowering the carbon footprint of corn dry milling and associated ethanol production. The invention provides for the efficient use of our natural gas resources to enable distributed power production through the application of industrial gas turbine cogeneration (combined heat and power, or CHP). In addition to being more energy-efficient, distributed CHP production can help reduce the electricity load on the current, stressed national-power grid, while at the same time avoiding the need to build new, centralized less-energy-efficient power-generating capacity to meet the growth in national power demand.

Some variations of the invention can be understood with reference to FIG. 1, which is a block-flow diagram depicting integration of corn fractionation, ethanol production, and edible corn oil recovery, optionally using carbon dioxide derived from the sugar fermentation to ethanol (or another fermentation product).

Since ethanol production involves the conversion of the starch component of the corn kernel to ethanol, it is desirable to remove as much of the non-starch components of the corn kernel as is practically and economically possible prior to the saccharification/fermentation of the remaining endosperm. Any known corn-fractionation method may be employed. In some embodiments, corn fractionation may be utilized as described in U.S. Pat. No. 7,938,345, Crown Iron Works (Roseville, Minn., US). The corn may be mildly steeped (tempered) prior to fractionation. Preferably, the fractionation unit is configured to substantially separate the germ and the bran from the endosperm, to generate a starch-rich stream containing at least 95% (such as about 98%) of the starch contained in the starting corn.

The co-product streams created by fractionation of the corn are a bran-like high fiber fraction and a germ-like high oil fraction. The bran is rich in fiber, such as about 60-75 wt % fiber. Removal of these two low-starch fractions significantly reduces the non-reactive biomass load on the downstream ethanol production process, particularly in the fermentors, the distillation column, and the distillers' dried grain with solubles (DDGS) dryer.

At least part of the starch stream (starch-rich stream in FIG. 1) is preferably conveyed, in the form of an aqueous slurry, to a saccharification unit configured to hydrolyze the starch into glucose. The glucose is introduced, either directly or after some period of storage, to an aqueous fermentor containing a microorganism to ferment glucose into dilute ethanol and carbon dioxide.

In other embodiments similar to FIG. 1, the fermentation product is a different alcohol, such as isobutanol, or another fermentation product. For example, the fermentation product may be selected from the group consisting of alcohols, organic acids, amino acids, enzymes, microorganisms, and combinations thereof. Exemplary fermentation products include, but are not limited to, ethanol, isopropanol, 1-butanol, isobutanol, lactic acid, succinic acid, 3-hydroxypropionic acid, lysine, aspartic acid, and so on.

Dilute ethanol is produced from fermentation and introduced to a distillation unit configured to generate an ethanol-rich overhead and a solids-rich still bottoms. The "distillation unit" may include one, two, or more distillation columns. The ethanol-rich overhead is sent to an ethanol drying unit, such as molecular sieves, configured to generate anhydrous ethanol. Anhydrous alcohol refers to fuel ethanol with a low water content, such as about 1 vol % or less.

Ethanol fermentation produces a large quantity of gaseous carbon dioxide ($CO_2$). In some embodiments, all or part of this carbon dioxide may be captured to be used as a solvent or co-solvent for extraction/recovery of edible corn oil from the corn germ co-product stream. When $CO_2$ is used as an extraction solvent or co-solvent, it may first be compressed, liquefied, or made supercritical.

During extraction, the $CO_2$ may be serving as a true solvent and/or as a physical aid to allow oil separation from the germ, and/or some other mechanism. In certain embodiments, a co-solvent with $CO_2$ is employed. The co-solvent may be, for example, ethanol or hexane.

In certain embodiments, the solvent for extraction of edible corn oil consists of liquefied $CO_2$ derived from fermentation. Thus the solvent used for extraction and the material to be extracted may be derived from the same source of annually renewable biomass. Typically, less than all of the $CO_2$ from fermentation will be liquefied to be used for oil extraction.

Extraction may be conducted batch-wise, continuously, or semi-continuously. Any known extraction unit may be employed, such as a hydraulic press, continuous screw press, multistage belt-type extractor, continuous counter-current immersion extractor, continuous two-stage percolation extractor, or rotary-type continuous extractor. In some embodiments, a combination of high-pressure continuous screw pressing with injection of liquid carbon dioxide can extract edible corn oil from flaked and/or conditioned corn germ. Following extraction, $CO_2$ may simply be vented.

After pressing or otherwise removing most of the corn oil using $CO_2$, the remaining solid material may be ground into a solvent-extracted meal as a high-protein co-product, if desired. The meal does not require desolventizing because the residual $CO_2$ in the meal will be very low, and the meal also does not require drying. An exemplary solvent-extracted meal composition produced by the disclosed process will be about 27 wt % starch, about 4 wt % oil, about 17 wt % protein, and about 51 wt % fiber (including ash), where all weight percentages are on a dry basis. In some embodiments, the solvent-extracted meal contains about 10 wt %, about 5 wt %, about 4 wt %, about 3 wt %, about 2 wt %, about 1 wt %, or less, oil in the meal.

Note that some of the process steps may be performed in separate locations. For example, the processing of the germ-rich stream may be conducted at another site. Thus, in some embodiments, FIG. 1 is practiced in a distributed manner across multiple locations.

Figure 2:
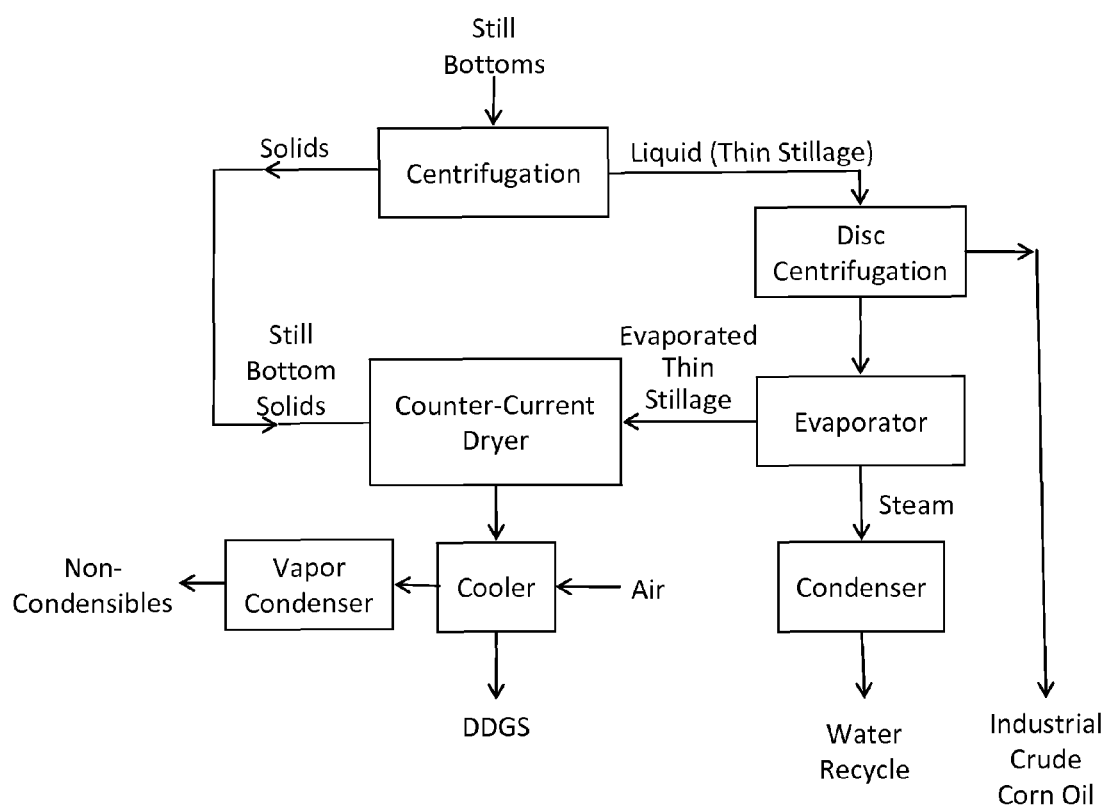
FIG. 2 depicts some variations of the invention utilizing a counter-current dryer for drying a DDGS co-product.

Some variations of the invention, including the aforementioned variations, can be understood with reference to FIG. 2, which is a block-flow diagram depicting the processing of still bottoms (such as, but not limited to, still bottoms produced in the process of FIG. 1). In FIG. 2, still bottoms are converted into DDGS, industrial crude corn oil, and water for recycling in the overall process.

The process shown in FIG. 2 includes a counter-current dryer (labeled as "Counter-Current Dryer" in the figure). The still bottoms solids (from the centrifuge in FIG. 2) and the evaporated thin stillage (from the disc centrifuge in FIG. 2) are fed to the counter-current dryer. Heated air is the main drying gas, although other gases and some steam will typically be present in the drying gas. The heated air passes counter-currently relative to the solids through the dryer. In some embodiments employing a vertically stacked counter-current dryer, a stacked heating chamber results in a relatively compact dryer with reduced heat losses through the walls, floor, and top of the dryer housing.

In some embodiments, the dryer is stacked on top of the cooler so that efficient drying and cooling of the solids can be accomplished. Thus some embodiments employ a vertically stacked, counter-current dryer/cooler combination. Preferably, air is used to fluidize the dryer but it will be appreciated that technically speaking, other fluids may be used. The drying fluid may include one or more gasses selected from the group consisting of air, nitrogen, $N_2/O_2$ mixtures, carbon dioxide, steam, and combinations thereof. Process control may be implemented to achieve a desired level of drying.

The mass of DDGS to be dried after fractionation of the corn will be much less than the mass to be dried in conventional processes, requiring less energy per unit of corn input. For example, the mass of DDGS to be dried in various embodiments of this invention may be reduced by about 25%, 40%, 50%, 60%, or more, compared to conventional processes. Further, the use of a counter-current, stacked dryer will greatly improve both energy use per unit of feed to the dryer as well as improving residual ethanol removal from the DDGS material to be dried. An exemplary composition of the DDGS produced by this process is about 10 wt % starch, about 13 wt % oil, about 46 wt % protein, and about 32 wt % fiber (including ash), where all weight percentages are on a dry basis. Other embodiments produce DDGS with higher than 46 wt % protein and/or lower than 10 wt % starch and/or lower than 13 wt % oil. The DDGS may contain, for example, about 12 wt %, about 10 wt %, about 7 wt %, about 5 wt %, or less of oil.

In certain embodiments, a portion or all of the bran separated from the corn (FIG. 1) may be blended with the still bottoms prior to drying, or introduced directly into one of the evaporation or drying units (such as the counter-current dryer). When this option is employed, the resulting DDGS product will contain more fiber from the bran. For example, the DDGS product may contain about 14 wt % starch, about 10 wt % oil, about 34 wt % protein, and about 42 wt % fiber.

As shown in FIG. 2, in some embodiments, industrial crude corn oil may be produced. Crude corn oil may optionally be recovered from thin stillage produced from the liquid phase of the bottoms from the distillation column by applying the well-known practice of separating oil from an aqueous stream using a disc centrifuge. The corn germ oil quality of this stream is typically only suitable for industrial applications, and is no longer suitable for edible purposes, without further treatment which would impose an economic penalty. It is noted that in preferred embodiments, corn fractionation removes most of the oil with the germ. Thus, there typically would not be a large amount of oil to recover as industrial crude corn oil.

In some embodiments, the process does not include a separate recovery scheme for industrial crude corn oil. Rather, the remaining corn oil (following fractionation and separation of the germ, such as in FIG. 1) is allowed to remain with the DDGS. Depending on the animal species being fed, and its age, some fat is added to almost all feeds. A DDGS product containing some corn oil may avoid or reduce the need to add fats or oils to the DDGS before use in animal feeds.

The water in the exhaust gases from the stacked, counter-current dryer may be largely condensed and returned (recycled) to the front end of the process to optionally create the slurry with the endosperm fraction (from fractionation) going to saccharification and fermentation. Water may be recycled for a variety of process uses. Also, any recovered residual ethanol from the exhaust gases may increase the overall ethanol yield, rather than burning the evaporated ethanol in a regenerative thermal oxidizer as is the current practice.

Figure 3:
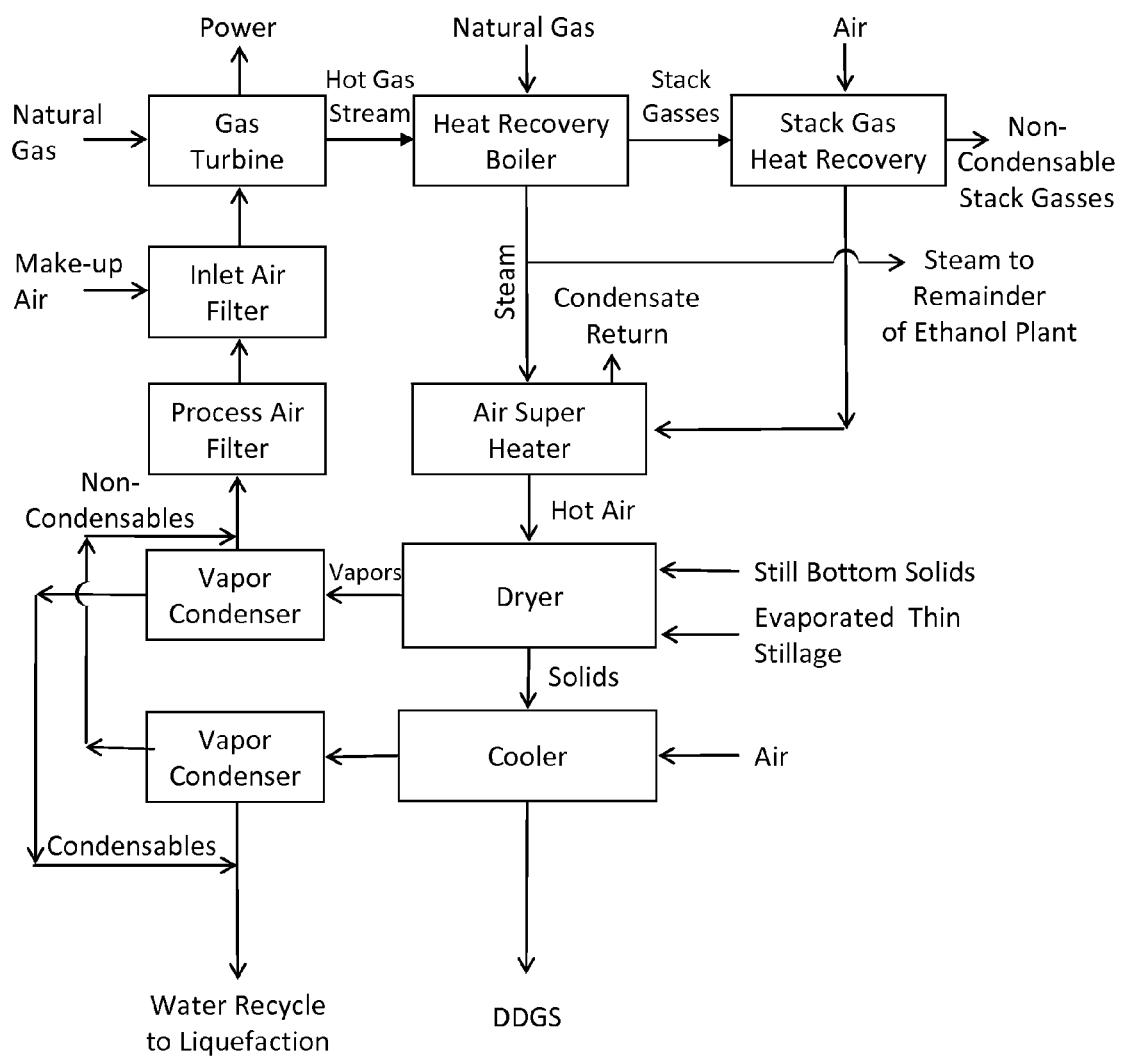
FIG. 3 depicts some variations of the invention utilizing integrated combined heat and power with a stacked counter-current dryer/cooler.

Some variations of the invention, including (but not limited to) the aforementioned variations in FIG. 1 or 2, can be understood with reference to FIG. 3. In FIG. 3, a dryer for drying DDGS is integrated with a natural gas-fired, turbine-based combined heat and power system to co-produce electricity in a biorefinery process. The gas turbine may be connector to a generator, using well-known methods, to generate electricity for internal use. Electricity may alternatively, or additionally, be exported to the grid or directly to a third-party user, such as a site partner.

FIG. 3 indicates that air is introduced in several locations within the process. It is preferred to utilize air, which for present purposes includes a gas that is substantially air, recognizing that other gasses may be present in the air. Any of the air feed streams may include non-condensables, such as carbon dioxide, or condensables, such as steam. The oxygen in the air is utilized for combustion with natural gas in the gas turbine. The present invention achieves good energy efficiency by using air for process heat recovery, DDGS drying, and power production in an integrated way.

In other embodiments, pure oxygen or oxygen-enriched air is introduced within the process, such as by direct injection into the gas turbine. However, this option can reduce the overall efficiency since air would need to be first separated into $O_2$ and $N_2$. For the purposes of this disclosure, oxygen-enriched air having any bounded, non-zero $O_2/N_2$ ratio is regarded substantially as "air."

In some embodiments, the non-condensable component of the exhaust gases from the dryer will be fed, such as via an inlet air filter, to the gas turbine. This approach can help ensure that substantially no VOCs can escape the process, which will help comply with U.S. EPA regulations. Additionally, the amount of residual ethanol lost from the drying of DDGS may be greatly reduced compared to conventional processes, in some embodiments of the invention.

The exhaust gases from the gas turbine are fed to a heat-recovery boiler, which can produce steam for process uses elsewhere in the plant. Additional natural gas is optionally introduced into the heat-recovery boiler, depending on the steam needs of the plant. In some embodiments, steam and/or power may be exported to users outside of the plant.

With continuing reference to FIG. 3, the stack gasses (process side) from the heat-recovery boiler are fed to a stack gas heat recovery unit, wherein air is introduced and heated by direct or indirect heat exchange with the hot stack gasses. Heated air is conveyed to an air superheater, which is heated using steam from the heat-recovery boiler, to produce hot air (which may be superheated) for the dryer. Non-condensable stack gasses are purged from the stack gas heat recovery unit.

Still bottom solids and/or evaporated thin stillage are fed to the dryer, along with the hot air derived from the air superheater. Solids from the dryer are cooled with air in a cooler (FIG. 3), to produce a DDGS product. The dryer may be, in some embodiments, a vertically stacked counter-current dryer. Other dryers as known in the art may be employed, such as but not limited to rotary drum dryers, flash dryers, steam tube dryers, fluidized-bed dryers, etc.

The vapor stream from the cooler is sent to a vapor condenser, wherein non-condensables are sent to a process air filter and condensables may be used as recycle water, such as for liquefaction. Vapors from the counter-current dryer are sent to a vapor condenser, which may be the same as or different from the vapor condenser for vapors from the cooler. Non-condensables from the counter-current dryer are sent to a process air filter. Condensables may be used as recycle water, such as for liquefaction.

The gas turbine in FIG. 3, as well as the heat-recovery boiler, may each be fired with fuels other than natural gas, if desired. Other fuels that may be used in either of these units include, but are not limited to, $C_1$-$C_5$ hydrocarbons, LPG, syngas, synthetic natural gas, lignin, biochar, or any other suitable fuel derived from biomass or a non-biomass source. The gas turbine is preferably operated in a fuel-lean, oxygen-rich regime when at steady state.

Process integration is an important feature of FIG. 3. Note that the fuel that is fed to the gas turbine is combusted using oxygen derived at least in part from the drying gas introduced to the stack gas heat recovery unit and/or from the cooling gas introduced to the cooler. In some embodiments, air is sequentially employed for process heat recovery, DDGS drying, and power production. Make-up air, shown in FIG. 3, may be necessary in some embodiments. In other embodiments, sufficient air is introduced into upstream heat recovery and/or in the cooler such that no make-up air is needed.

There are many benefits to this integrated process approach when producing ethanol as the primary product via corn dry milling. The disclosed process can produce more edible corn oil than conventional processes. There is no need to use hexane or other hydrocarbon solvents to produce edible corn oil. The process can produce a high-protein, solvent extracted meal, which can be more widely applied to monogastric animal feed diets (e.g. poultry and hogs). The process reduces residual ethanol (a VOC) in the DDGS.

The DDGS product that can be produced using the present invention has several advantages over convention DDGS. In particular, high protein levels and low fiber levels may be associated with DDGS compositions produced. These characteristics increase potential application and value.

Additionally, fractionation as described herein can solve a problem of mycotoxin contamination of DDGS. Mycotoxins in corn are produced by certain molds which infect the ears of corn. Global warming may cause significant mycotoxin contamination of corn to move north into the current U.S. corn belt. Mycotoxin contamination is the reason corn is not currently grown further south in the U.S. Any product that has above a certain level of mycotoxins (e.g. aflatoxin, deoxynivalenol, fumonisin, or zearalenone) cannot be used as animal feed. See Patience and Ensley, "Mycotoxin Contamination of Corn," Iowa State University, IPIC 12 Mar. 2010, which is incorporated by reference herein for its teachings of mycotoxin contamination and certain concentrations in animal feed. These or other mycotoxin concentrations may be selected for process control and DDGS quality assurance.

Any mycotoxin on the surface of the corn kernel will be concentrated in the DDGS by a factor of about 3 going through conventional corn dry milling. In the present invention, using fractionation, mycotoxins (if present) will be concentrated in the bran, and not in the DDGS. Adjusting the process to separate out more bran will also tend to reduce mycotoxin concentration in the DDGS. Avoiding mycotoxin contamination of the DDGS is another means of enhancing the value of the DDGS product.

Importantly, the present invention can greatly reduce the energy usage and carbon footprint in the process of producing ethanol from corn by optimizing and integrating the unit operations, including cogeneration.

Engineering optimization can be conducted to achieve further energy integration. For example, energy requirements can be reduced by combining portions of streams from individual processes into a single unit. Various levels of heat recovery can be employed to meet drying requirements.

It will be recognized that while the present invention has been described with reference to ethanol as the primary product, the principles of the invention also apply to any other product that can be produced by fermenting sugars.

This invention is capable of economically producing ethanol, DDGS, corn bran, corn germ, edible corn oil, industrial crude corn oil, solvent-extracted meal, carbon dioxide, electricity, and steam (which optionally may be exported to a third party). There are many known market uses and applications for the various co-products that may be produced. The applications include food, feed, fuel, and chemical/material uses for these products.

For example, the edible corn oil can be sold for food uses while the industrial crude corn oil can be utilized for producing biodiesel or for industrial uses such as rubber substitutes, rust preventatives, inks, textiles, soaps, and insecticides. Electricity may be exported, such as sold to the grid, or sold over the fence to a co-located partner, for example.

Also, because this process has a reduced carbon footprint and reduced $CO_{2e}$ emissions, regulated market mechanisms such as renewable-energy certificates (RECs) or renewable identification numbers (RINs) may be generated in connection with the production of any of the products.

All publications, patents, and patent applications cited in this specification are incorporated herein by reference in their entirety as if each publication, patent, or patent application was specifically and individually put forth herein.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially. All references to a "unit" include multiple subunits (e.g., columns, vessels, or reactors) within the unit, or multiple instances of the same unit.

Therefore, to the extent that there are variations of the invention, which are within the spirit of the disclosure or equivalent to the inventions found in the appended claims, it is the intent that this patent will cover those variations as well. The present invention shall only be limited by what is claimed.

What is claimed is:

1. A process for producing ethanol, corn oil, and DDGS from corn, said process comprising:
    (a) introducing corn to a corn fractionation unit configured to substantially separate the germ and the bran from the endosperm, to generate a starch stream containing up to 98% of the starch contained in said corn;
    (b) introducing at least a portion of said starch stream, in the form of an aqueous slurry, to a saccharification unit configured to hydrolyze said starch into glucose;
    (c) introducing at least a portion of said glucose to an aqueous fermentor containing a microorganism to ferment glucose into dilute ethanol and carbon dioxide;
    (d) introducing said dilute ethanol to a distillation unit configured to generate an ethanol-rich distillate (overhead) and a solids-rich still residue (still bottoms);
    (e) introducing said ethanol-rich overhead to an ethanol drying unit configured to generate anhydrous ethanol;
    (f) introducing at least a portion of said germ, or a conditioned form thereof, to an extraction unit configured to extract edible crude corn oil using a solvent;
    (g) drying said solids-rich still residue using a drying gas in a counter-current dryer disposed in a vertically stacked dryer, to generate a dried solids stream;
    (h) cooling said dried solids stream using a cooling gas in a cooler disposed in communication with said vertically stacked dryer, to generate a cooled solids stream comprising distillers' dried grains with solubles (DDGS); and
    (i) recovering said anhydrous ethanol, said edible crude corn oil, and said DDGS,
    wherein said DDGS has higher nutritional value than DDGS produced by an otherwise-equivalent process that does not utilize said vertically stacked dryer.

2. The process of claim 1, said process further comprising generating a solvent-extracted meal from said germ.

3. The process of claim 1, wherein said solvent comprises at least a portion of said carbon dioxide from step (c).

4. The process of claim 3, wherein said solvent comprises liquefied carbon dioxide derived at least in part from said carbon dioxide from step (c).

5. The process of claim 1, wherein said extraction unit utilizes mechanical pressing.

6. The process of claim 5, wherein said extraction unit is a high-pressure, continuous screw press with one or more injection ports for introducing said solvent.

7. The process of claim 1, wherein said edible crude corn oil contains about 100 ppm or less phospholipids.

8. The process of claim 1, wherein mycotoxins, if any, that are present on the outside of the corn kernel are concentrated in said bran rather than in said DDGS as a result of separating said bran from said endosperm in said corn fractionation unit.

9. The process of claim 1, said process further comprising blending at least a portion of said bran with said solids-rich still bottoms prior to, or during, step (g).

10. The process of claim 1, said process further comprising recycling or recovering at least a portion of exhaust gases from said counter-current dryer, wherein said recycling or recovering includes (i) recycling water back to step (b) and/or step (c) and/or (ii) recovering ethanol and optionally recycling said ethanol back to step (d) and/or step (e).

* * * * *